(12) United States Patent
Roeder

(10) Patent No.: US 9,827,124 B2
(45) Date of Patent: Nov. 28, 2017

(54) MAGNETIC HANDLE ASSEMBLY FOR PROSTHESIS DELIVERY DEVICE

(71) Applicant: Cook Medical Technologies LLC, Bloomington, IN (US)

(72) Inventor: Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 292 days.

(21) Appl. No.: 14/882,530

(22) Filed: Oct. 14, 2015

(65) Prior Publication Data

US 2016/0158041 A1    Jun. 9, 2016

Related U.S. Application Data

(60) Provisional application No. 62/088,273, filed on Dec. 5, 2014.

(51) Int. Cl.
*A61F 2/966* (2013.01)
*A61F 2/95* (2013.01)
*A61F 2/86* (2013.01)

(52) U.S. Cl.
CPC .................. *A61F 2/95* (2013.01); *A61F 2/86* (2013.01); *A61F 2/966* (2013.01); *A61F 2002/9505* (2013.01); *A61F 2002/9517* (2013.01); *A61F 2002/9522* (2013.01); *A61F 2002/9665* (2013.01)

(58) Field of Classification Search
CPC .... A61F 2/2427; A61F 2/2436; A61F 2/2439; A61F 2/95; A61F 2/954; A61F 2/962; A61F 2/966; A61F 2002/9505; A61F 2002/9511; A61F 2002/9517; A61F 2002/9665
See application file for complete search history.

(56) References Cited

U.S. PATENT DOCUMENTS 5,147,370 A * 9/1992 McNamara ............... A61F 2/88
606/108
5,476,505 A * 12/1995 Limon ....................... A61F 2/88
604/109

(Continued)

OTHER PUBLICATIONS

Extended European Search Report for corresponding EP 15275247, dated Feb. 1, 2016, 8 pages.

*Primary Examiner* — Ryan J Severson
(74) *Attorney, Agent, or Firm* — Brinks Gilson & Lione

(57) ABSTRACT

A prosthesis delivery comprising a rotatable inner cannula and a prosthesis releasably coupled to a proximal end of the inner cannula is disclosed. The inner cannula has a first position in which the prosthesis is retained on the cannula and a second position in which the prosthesis is released. At least one magnet is disposed on the inner cannula. A handle assembly is disposed about a distal portion of the inner cannula, the handle assembly comprising a rotary collar having at least one magnet disposed on the inner surface thereof, wherein the at least one magnet disposed on the rotatable inner cannula and the at least one magnet disposed on the inner surface of the rotary collar comprise a magnetic attraction. The magnetic attraction translates torque from rotation of the rotary collar to rotate the inner cannula from the first position to the second position to thereby release the prosthesis.

9 Claims, 10 Drawing Sheets

(56) References Cited

U.S. PATENT DOCUMENTS

| | | | |
|---|---|---|---|
| 5,480,423 A * | 1/1996 | Ravenscroft | A61F 2/90 606/194 |
| 5,797,952 A * | 8/1998 | Klein | A61F 2/88 606/198 |
| 5,824,058 A * | 10/1998 | Ravenscroft | A61F 2/90 606/194 |
| 6,413,269 B1 | 7/2002 | Bui et al. | |
| 6,623,518 B2 * | 9/2003 | Thompson | A61F 2/91 606/108 |
| 7,172,622 B2 * | 2/2007 | Weber | A61F 2/95 623/1.12 |
| 8,062,345 B2 * | 11/2011 | Ouellette | A61F 2/07 623/1.12 |
| 8,092,510 B2 * | 1/2012 | Metcalf | A61F 2/95 623/1.12 |
| 8,267,985 B2 * | 9/2012 | Garcia | A61B 17/12022 623/1.11 |
| 9,144,510 B2 * | 9/2015 | Havel | A61F 2/95 |
| 9,173,756 B2 * | 11/2015 | Hopkins | A61F 2/95 |
| 9,320,631 B2 * | 4/2016 | Moore | A61F 2/07 |
| 9,333,104 B2 * | 5/2016 | Ouellette | A61F 2/07 |
| 9,364,355 B2 * | 6/2016 | Hopkins | A61F 2/95 |
| 9,393,115 B2 * | 7/2016 | Tabor | A61F 2/2412 |
| 9,408,734 B2 * | 8/2016 | Arbefeuille | A61F 2/07 |
| 9,408,735 B2 * | 8/2016 | Arbefeuille | A61F 2/07 |
| 9,675,456 B2 * | 6/2017 | Quill | A61F 2/2436 |
| 2004/0087899 A1 | 5/2004 | Weber et al. | |
| 2005/0049674 A1 * | 3/2005 | Berra | A61F 2/07 623/1.13 |
| 2006/0271153 A1 * | 11/2006 | Garcia | A61B 17/12022 623/1.11 |
| 2007/0186933 A1 * | 8/2007 | Domingo | A61B 17/12022 128/207.15 |
| 2008/0294230 A1 * | 11/2008 | Parker | A61F 2/95 623/1.11 |
| 2009/0030497 A1 * | 1/2009 | Metcalf | A61F 2/95 623/1.12 |
| 2009/0192585 A1 * | 7/2009 | Bloom | A61F 2/2412 623/1.11 |
| 2009/0254165 A1 * | 10/2009 | Tabor | A61F 2/2412 623/1.11 |
| 2011/0251664 A1 | 10/2011 | Acosta De Acevedo | |
| 2012/0197379 A1 * | 8/2012 | Laske | A61F 2/2412 623/1.11 |
| 2013/0338787 A1 | 12/2013 | Hopkins et al. | |
| 2013/0338788 A1 * | 12/2013 | Hopkins | A61F 2/95 623/23.7 |
| 2013/0345789 A1 * | 12/2013 | Havel | A61F 2/95 623/1.12 |
| 2014/0128963 A1 | 5/2014 | Quill et al. | |
| 2014/0142680 A1 * | 5/2014 | Laske | A61F 2/2412 623/1.11 |
| 2016/0158041 A1 * | 6/2016 | Roeder | A61F 2/86 623/1.11 |
| 2016/0158050 A1 | 6/2016 | Skelton et al. | |

* cited by examiner

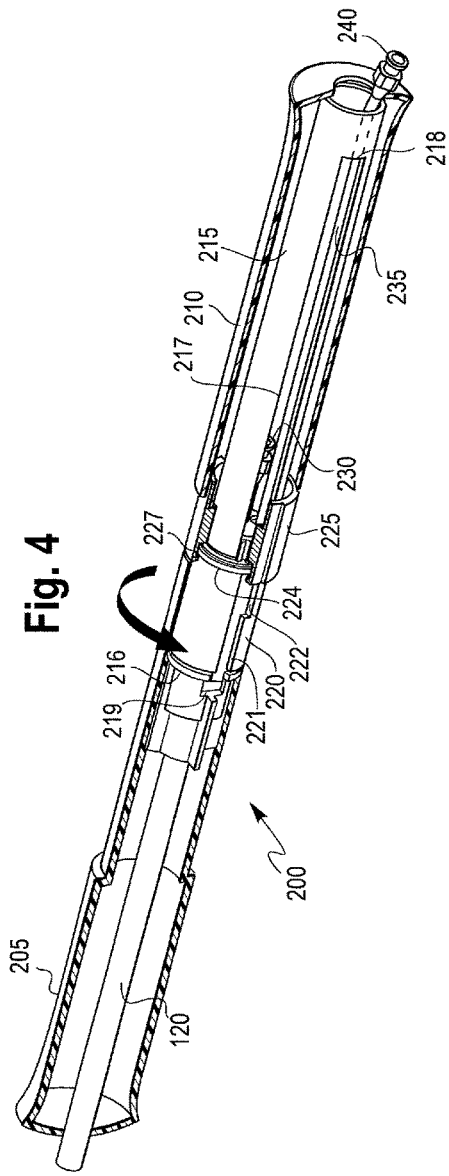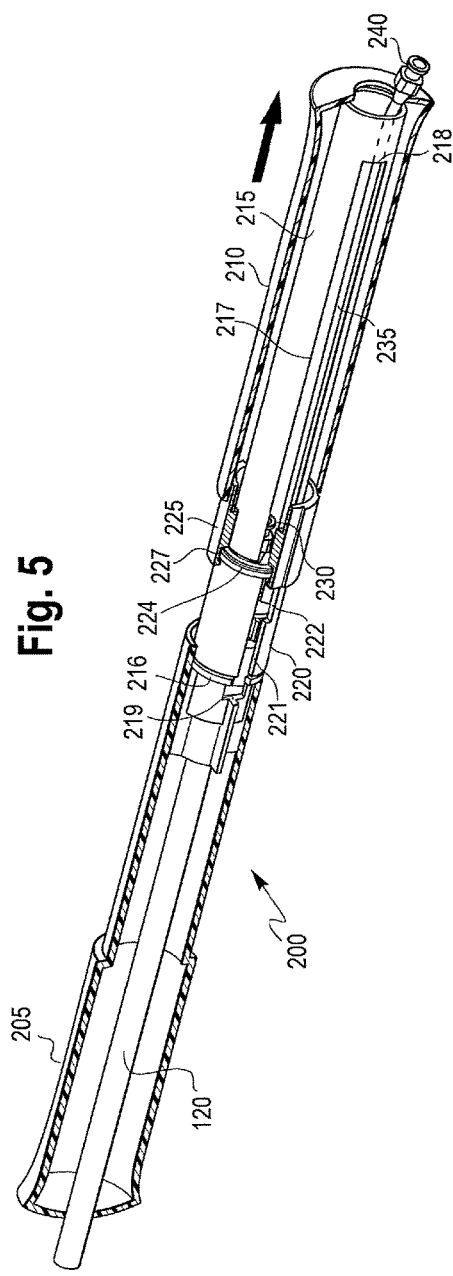

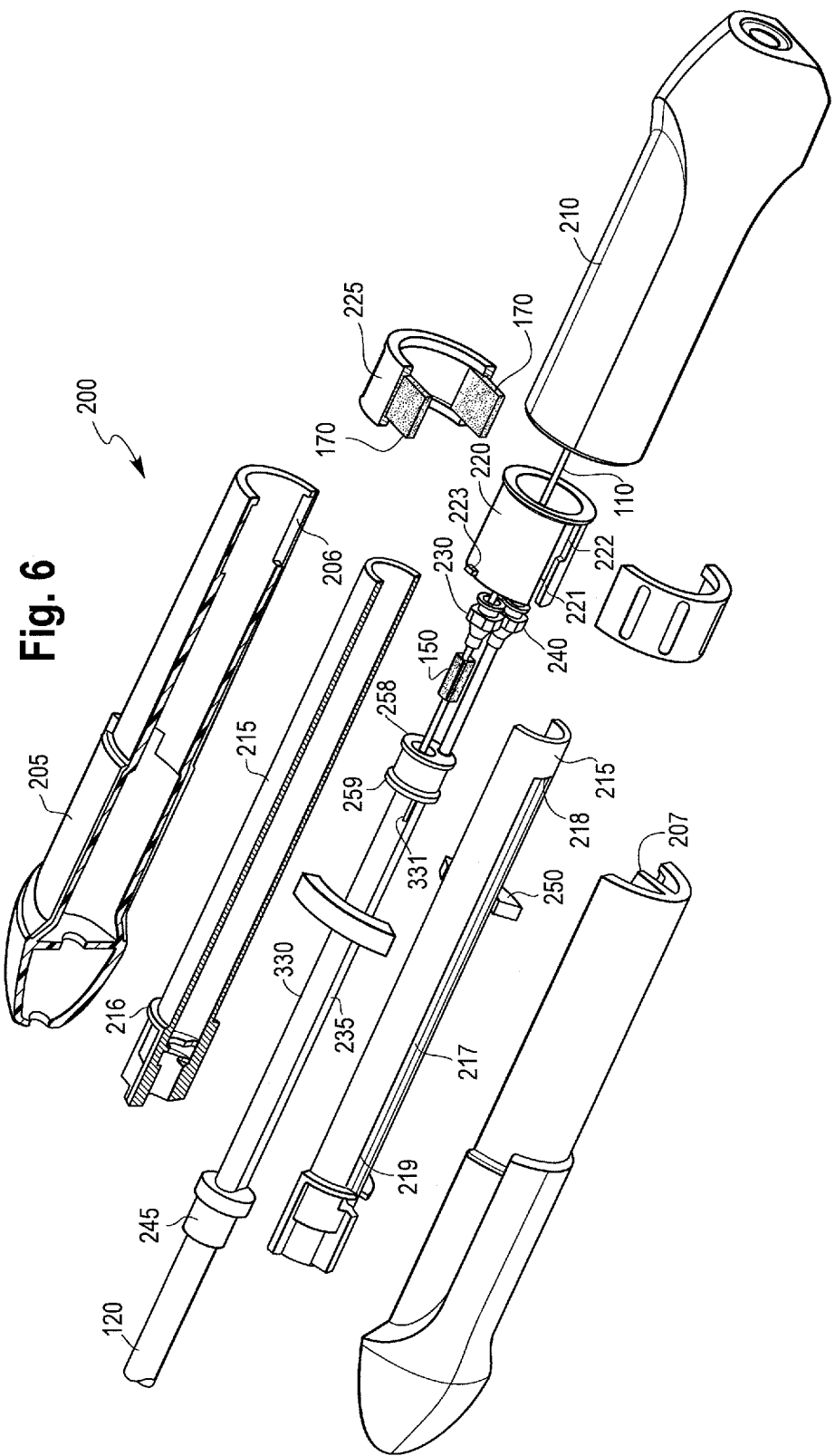

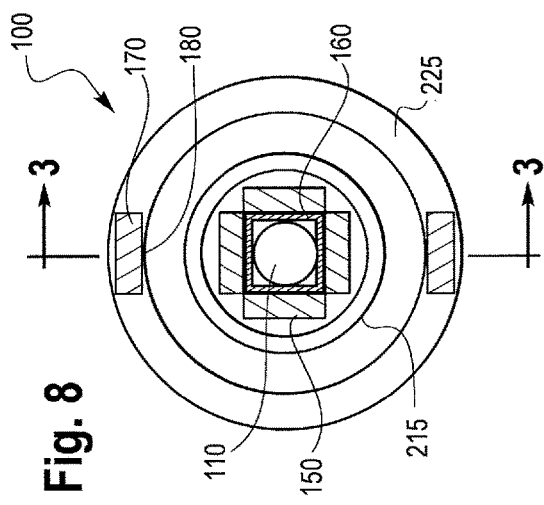
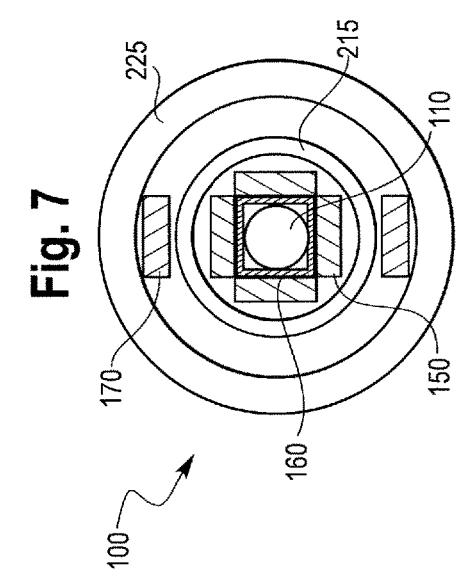
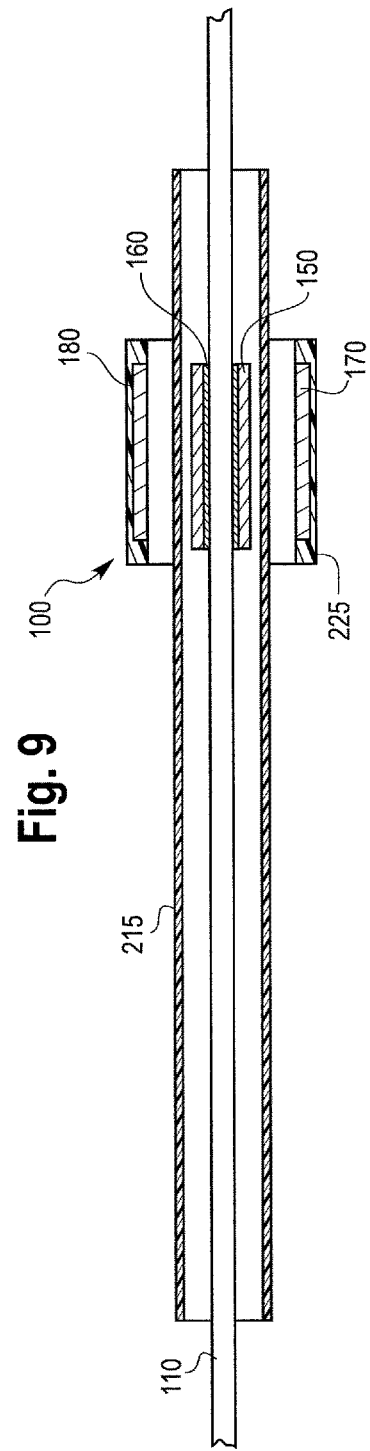

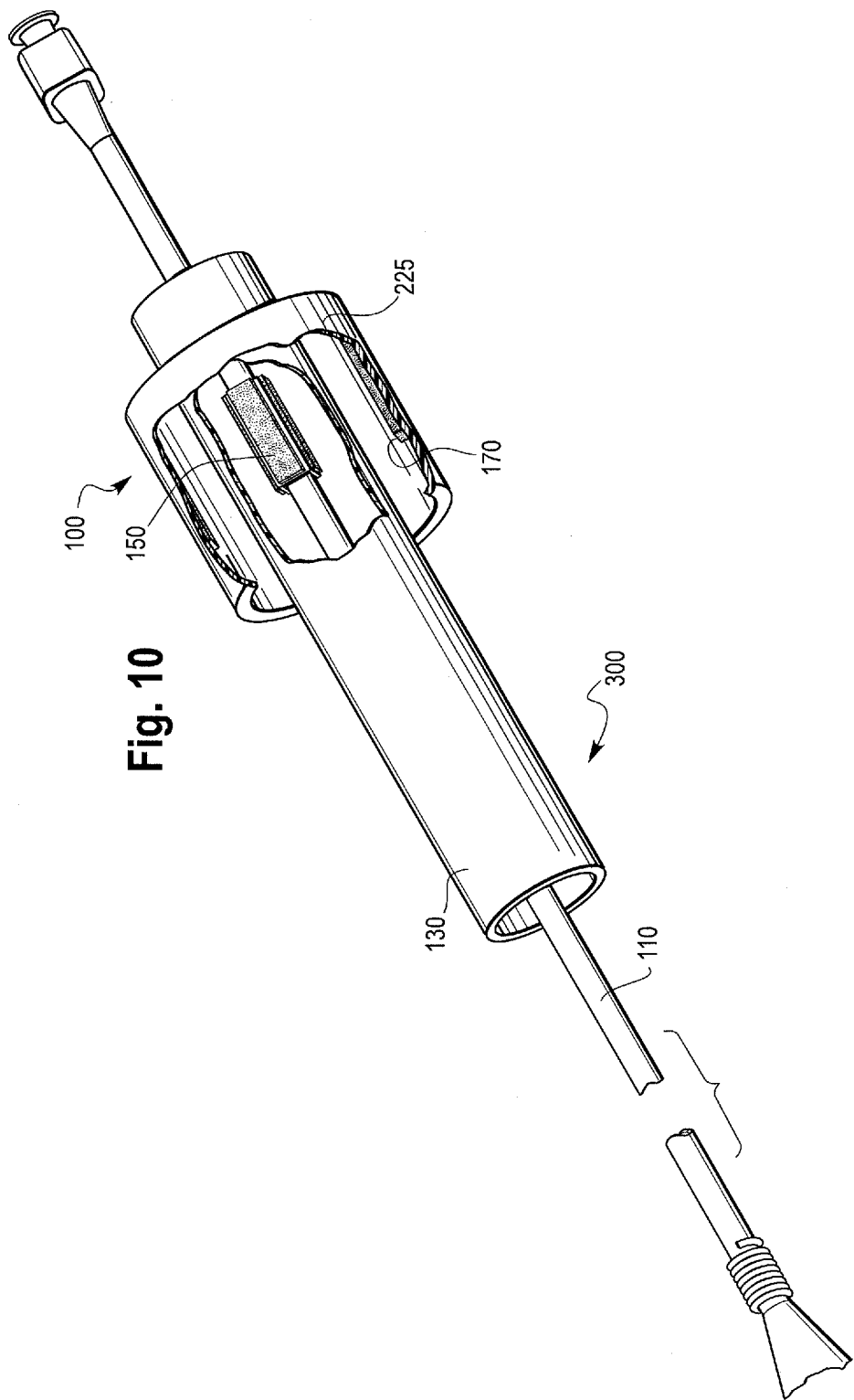

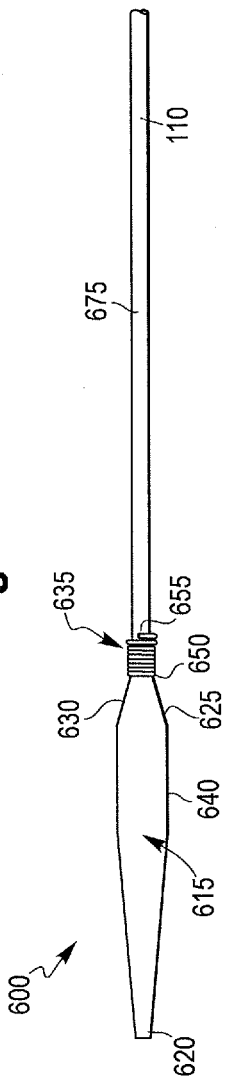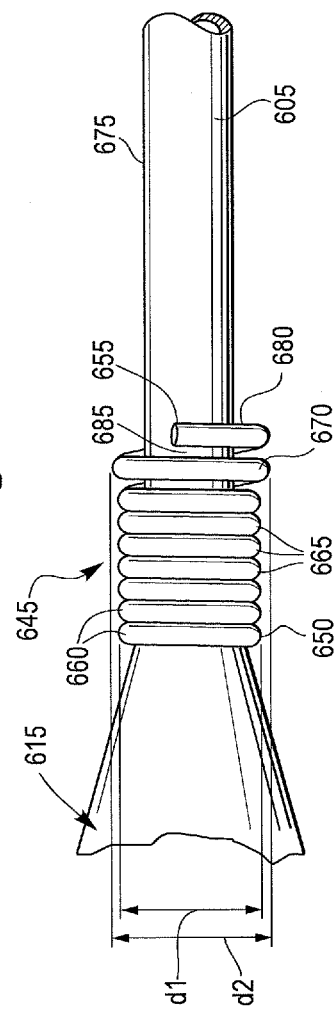

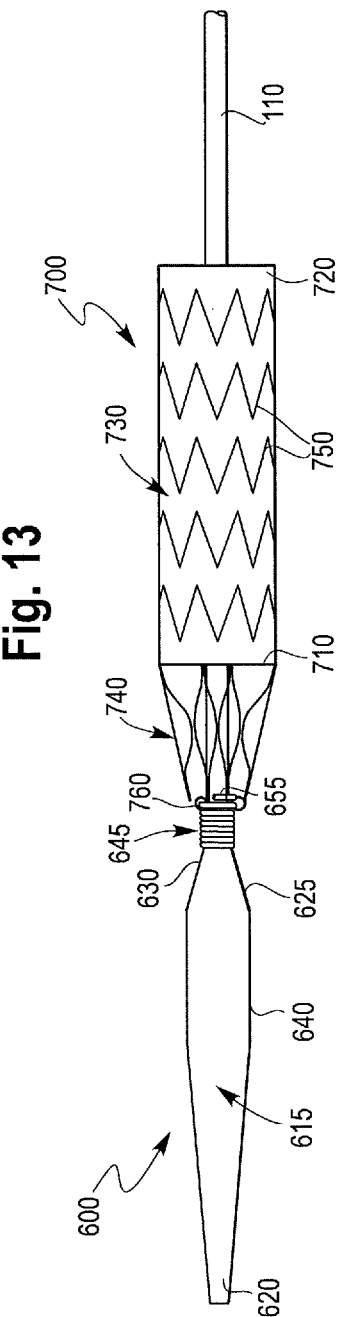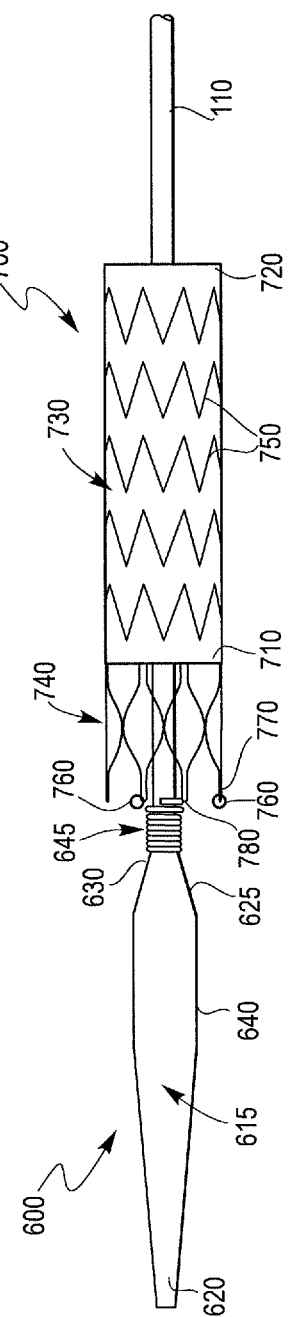

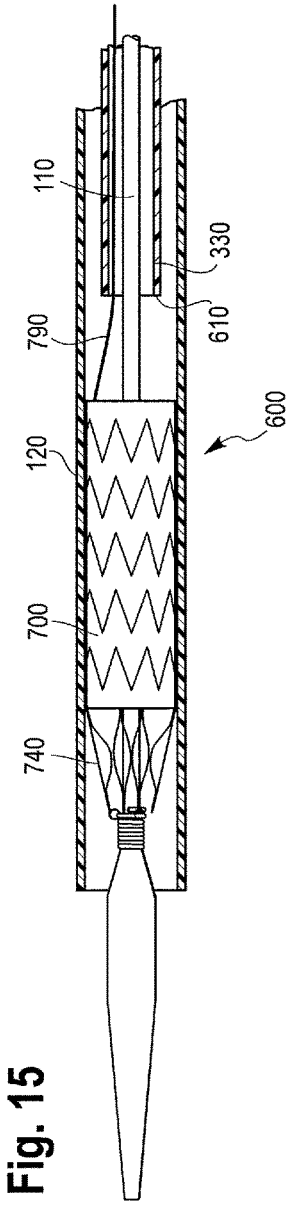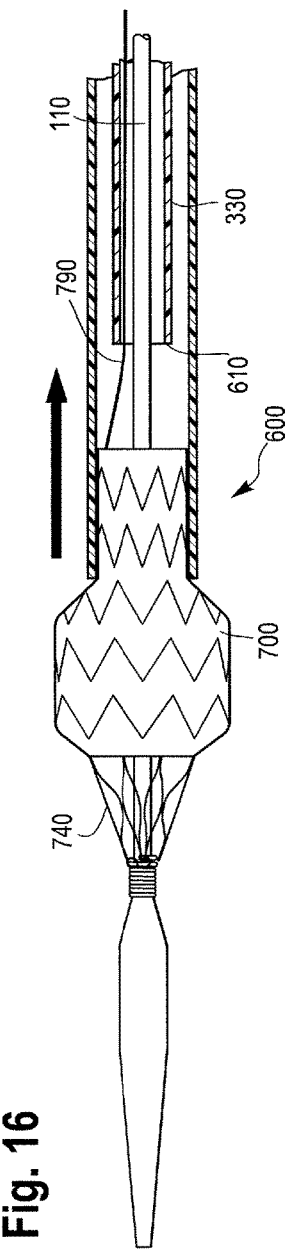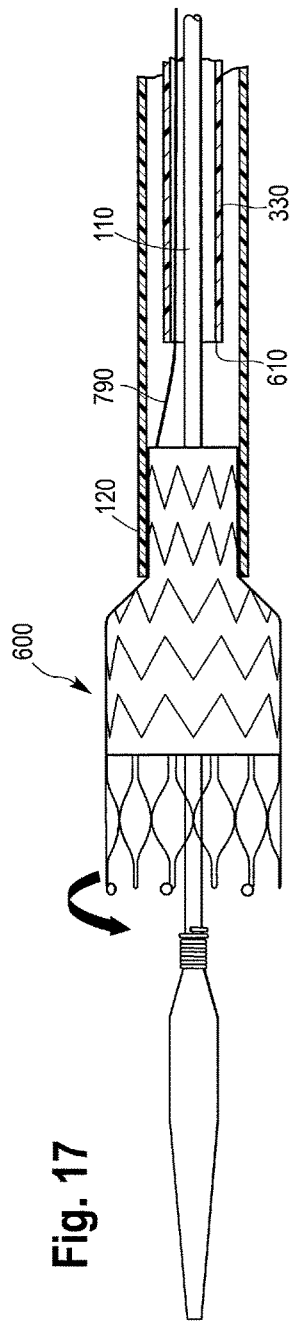

MAGNETIC HANDLE ASSEMBLY FOR PROSTHESIS DELIVERY DEVICE

RELATED APPLICATIONS

The present application claims the benefit of the filing date under 35 U.S.C. §119(e) of Provisional U.S. Patent Application Ser. No. 62/088,273 filed Dec. 5, 2014, which is hereby incorporated by reference.

BACKGROUND

The present invention relates to delivery devices for prostheses, such as stents, grafts and stent grafts (collectively prostheses) in the vascular system of a patient. In particular, the invention relates to a delivery device having a handle assembly with a rotational magnetic component that permits controlled and sequential release and deployment of a prosthesis from the delivery device.

The handle assembly of the delivery device is configured to prevent the user from performing deployment steps out of sequence while helping to ensure that all deployment steps are completed. Particularly, the handle assembly is designed to allow the user the ability to perform only one deployment step at a time, and until one step is completed, the next deployment step cannot be initiated and/or performed.

In one non-limiting example, when the delivery device is used to deliver a bifurcated stent graft in the aorta, it may be desirable to provide a handle assembly on a delivery device that facilitates deployment of the stent graft in a preferred sequence including partial sheath withdrawal to expose the proximal stent and contralateral stent limb, followed by deployment of the proximal stent, further sheath withdrawal to expose the ipsilateral limb and finally trigger wire release to facilitate deployment of the distal end of the stent graft.

One example of a handle assembly that may be used with a delivery device for the controlled and sequential deployment of a stent graft is Provisional U.S. Patent Application Ser. No. 62/087,457, filed on Dec. 4, 2014, entitled "Delivery Device Handle Assembly For The Sequential Deployment of a Prosthesis" which disclosure is incorporated by reference herein in its entirety.

The handle assembly of the delivery device described herein comprises a magnetic sub-assembly within the handle assembly to translate torque from a physician-actuated handle in order to rotate the cannula and thereby release a stent from the proximal end of the delivery device.

SUMMARY

A prosthesis delivery device is described. The device comprises a rotatable inner cannula having a proximal end and a distal end and at least one magnet disposed on the rotatable inner cannula. A prosthesis is releasably engaged with the proximal end of the inner cannula. A handle assembly is disposed about a portion of the rotatable inner cannula and comprises a rotary collar having an inner surface and at least one magnet disposed on the inner surface. The at least one magnet disposed on the rotatable inner cannula and the at least one magnet disposed on the inner surface of the rotary collar comprise a magnetic attraction, wherein the attraction translates torque from the rotation of the rotary collar to rotate the inner cannula to thereby release the prosthesis.

A method of releasing a prosthesis from a delivery device is also described. The delivery device comprises a rotatable inner cannula having a proximal end and a distal end and at least one magnet disposed on the inner cannula. A prosthesis is releasably engaged with the proximal end of the inner cannula and a handle assembly is disposed about a portion of the rotatable inner cannula. In one example, the method comprises retracting a portion of the handle assembly to expose a proximal portion of the prosthesis. The method further comprises rotating a rotary collar within the handle assembly, wherein the rotary collar comprises at least one magnet disposed on an inner surface thereof. A magnetic attraction between the at least one magnet disposed on the inner surface of the rotary collar and the at least one magnet disposed on the inner cannula translates torque from the rotation of the rotary collar to rotate the inner cannula to thereby release a proximal portion of the prosthesis. The method further comprises further retracting the portion of the handle assembly to thereby release a distal portion of the prosthesis.

BRIEF DESCRIPTION OF THE DRAWINGS

FIG. 4 is a partial sectional side view of a handle assembly of a delivery device of FIG. 1 during deployment of a prosthesis.

FIG. 5 is a partial sectional side view of a handle assembly of a delivery device of FIG. 1 during deployment of a prosthesis.

FIG. 6 is an exploded view of a handle assembly of a prosthesis delivery device of FIG. 1.

FIG. 7 is a cross-sectional view of one example of a magnetic sub-assembly within the handle assembly of FIGS. 1-6.

FIG. 8 is a cross-sectional view of another example of a magnetic sub-assembly within the handle assembly of FIGS. 1-6.

FIG. 9 is a side cross-sectional view of FIG. 8.

FIG. 10 is a cut away perspective view of the handle assembly illustrating the magnetic-sub assembly therein.

FIG. 11 is a side view of a proximal end of a prosthesis delivery device with an exemplary proximal stent attachment and release mechanism.

FIG. 12 is an enlarged side view of the proximal stent attachment and release mechanism of FIG. 11.

FIG. 13 is a side view of a delivery device having a prosthesis carried on the proximal end thereof with a proximal stent attached to the attachment and release mechanism.

FIG. 14 illustrates the prosthesis delivery device of FIG. 13 with the proximal stent released from the proximal attachment and release mechanism.

FIGS. 15-19 illustrate one example of a method for releasing a prosthesis from a delivery device.

DETAILED DESCRIPTION OF INVENTION

Figure 1:
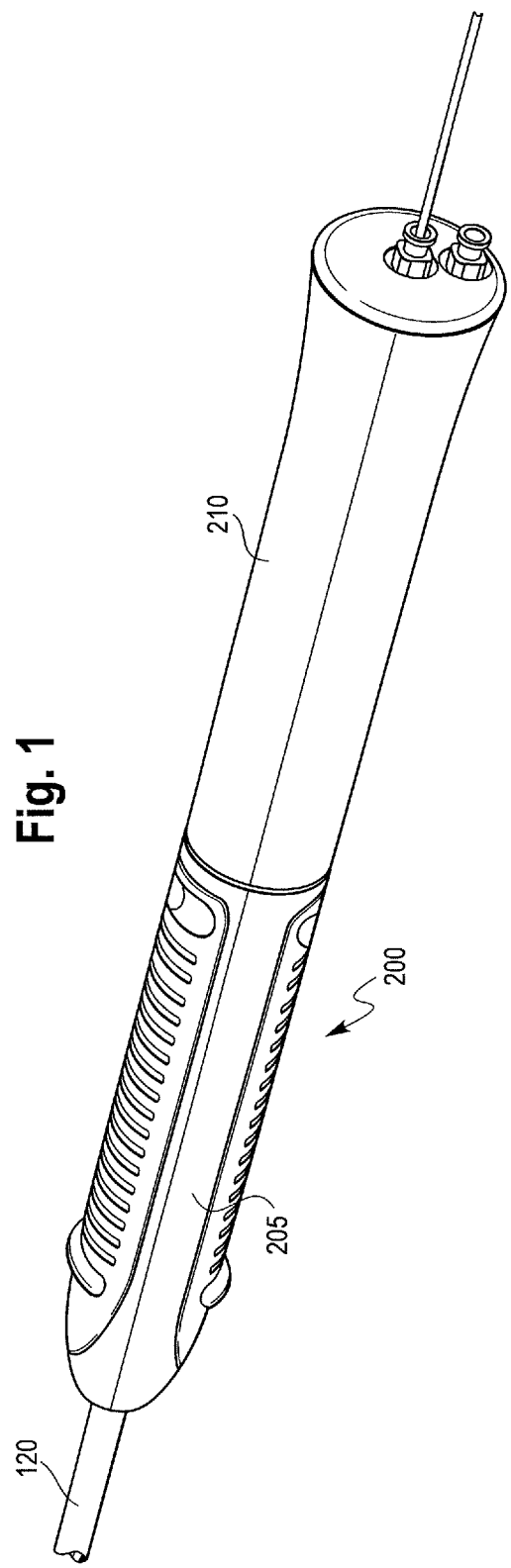
FIG. 1 is a rear perspective view of an example of a handle assembly of a prosthesis delivery device.

The embodiments described in this disclosure will be discussed generally in relation to deployment of prostheses, such as stents, grafts and stent grafts into the aorta, but the disclosure is not so limited and may be applied to other implantable prostheses that may be placed in other areas of the vasculature or other body vessels or lumens.

The term "proximal" refers to a direction that is generally closest to the heart during a medical procedure, while the term "distal" refers to a direction that is furthest from the heart during a medical procedure.

The term "stent graft" refers to a device that has a tubular body of biocompatible graft material and at least one stent fastened to the tubular body to define a lumen through the stent graft. The stent graft may be bifurcated and/or may include fenestrations, side arms, or the like. Other arrangements and configurations of stent grafts also are within the scope of this disclosure.

As shown and described more fully below, the delivery device described herein generally comprises a cannula 110 extending from a proximal end 600 to a handle assembly 200 located at its distal end. In one example, one or more magnetic components within the handle assembly 200 facilitate rotation of the cannula 110 when the handle is manually rotated by the user. For example, the respective magnets are attracted to each other, such as by a magnetic dipole-dipole interaction, to thereby translate torque created by the physician-actuated handle to rotate the cannula 110 and thereby release the stent from the delivery device.

FIGS. 1-6 illustrate an example of a delivery device with a handle assembly 200 located at the distal end thereof. The distal end of the device is intended to remain outside of the patient during a procedure. The handle assembly 200 is actuated by the physician to release a prosthesis from the proximal end 600 of the delivery device. Any portion of the handle assembly 200 and its various components may be provided with gripping features that provide secure and/or ergonomic gripping by the physician and provide the physician with tactile feedback while gripping and/or operating the handle. FIG. 6 illustrates an exploded view of the handle assembly 200 incorporating a magnetic sub-assembly 100, as will be described in further detail below.

FIGS. 2-5 illustrate the handle assembly 200 in various stages as it is operated by a user to sequentially release the proximal and distal ends of a prosthesis, such as a stent graft releasably attached to the cannula 110 at the proximal end 600 of the delivery device. A first handle 205 is a stationary proximal handle that allows the physician to grip and stabilize the delivery device. The first handle 205 is attached to a positioner 330 and provides a consistent point of reference for the prosthesis during a procedure. The second handle 210 is distal to the first handle 205 and is actuated by the physician during deployment of the prosthesis.

The handle assembly 200 further includes a locking mechanism 250 that is shown in FIG. 6. This locking mechanism 250 is disposed about the surface of the first handle 205 and prevents unintended or premature movement of the second handle 210 relative to the first handle 205. The locking mechanism 250 may engage the first handle 205 through latching or other engagement, including, but not limited to a pin, a clip and the like.

Figure 2:
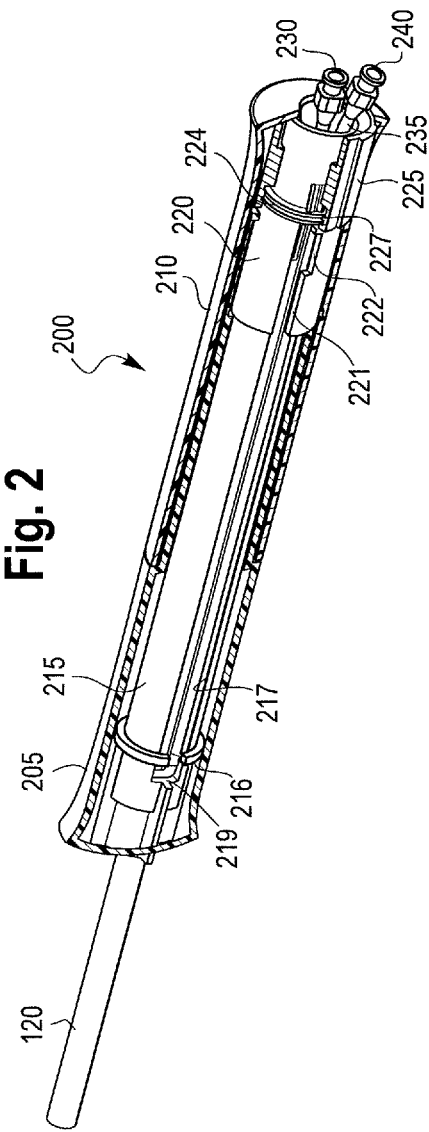
FIG. 2 is a partial sectional side view of a handle assembly of a delivery device of FIG. 1 during deployment of a prosthesis.

As illustrated in FIGS. 1 and 2, the first handle 205 is disposed at the proximal end of handle assembly 200 and about the distal end of a sheath 120. The first handle 205 extends the length of the deployment handle assembly 200 and defines a generally tubular interior space that houses other components of the handle assembly. The second handle 210 is partially disposed about the distal end of the first handle 205. When the second handle 210 is pulled distally from a first position (FIG. 2) to a second position (FIG. 3), the sheath 120 is at least partially withdrawn to expose a proximal portion of the prosthesis carried at the proximal end 600 of the device and, after the proximal end of the prosthesis is released, further pull back of the second handle 210 (FIG. 5) to a third position further withdraws the sheath 120 to release the distal end of the prosthesis.

To accomplish this, the second handle 210 is engageable with a handle rear inner 215, such that retraction of the second handle 210 in a distal direction also retracts the handle rear inner 215 relative to the first handle 205. As shown in FIG. 2, the handle rear inner 215 is initially positioned within the first handle 205 and is distally slidable relative to the first handle 205. The proximal end of the handle rear inner 215 is attached to the sheath 120 at the sheath connector 245. The handle rear inner 215 has a body slot 217 that extends along one side of the handle rear inner 215. The body slot 217 provides a track for a tab 207 (FIG. 6) that protrudes from an inner surface of the first handle 205 and prevents rotational movement of the handle rear inner 215. The proximal end 219 of the slot 217 limits the distal-most position of the handle rear inner 215 while the distal end 218 of the slot 217 limits the proximal most position of the handle rear inner 215. The handle rear inner 215 further includes a proximal lip 216 that limits the distal movement of the handle rear inner 215 and the attached second handle 210 when the proximal lip 216 encounters and/or abuts the proximal end of a rotary dial 220.

Figure 3:
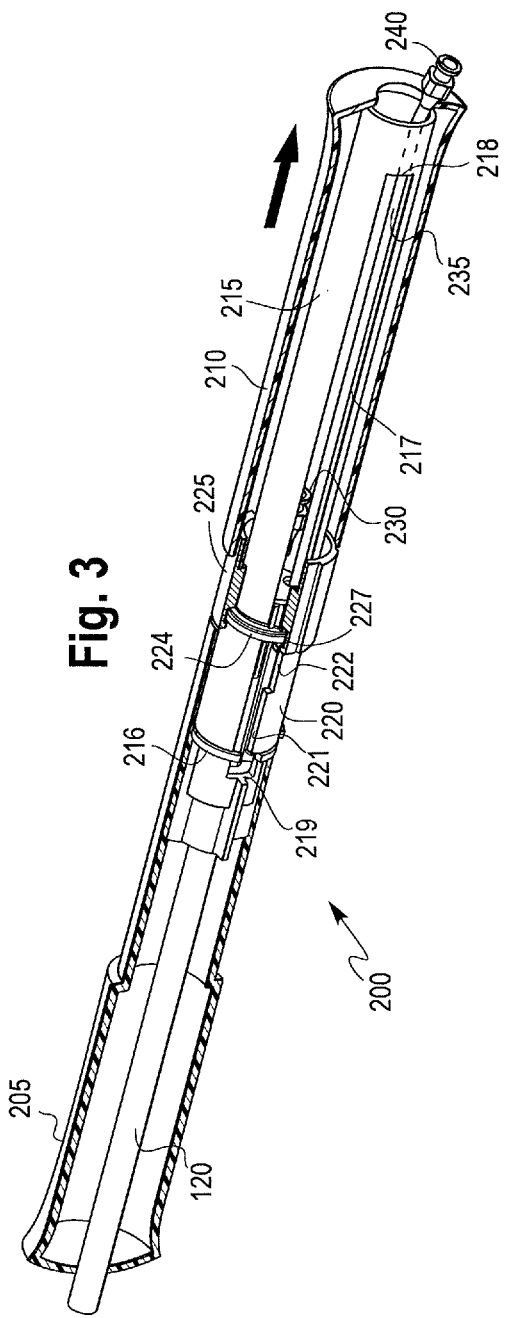
FIG. 3 is a partial sectional side view of a handle assembly of a delivery device of FIG. 1 during deployment of a prosthesis.

The rotary collar 225 is disposed about the handle rear inner 215. The proximal end of the rotary collar 225 can rotate about the distal end of the rotary dial 220. Specifically, as shown in FIG. 3, threading 224 of the rotary dial 220 engages the collar threading 227 located at the proximal end of the rotary collar 225. Rotary collar magnets 170 on the inside surface of the rotary collar 225 are magnetically attracted to cannula magnets 150 located on the inner cannula 110 which have an opposite polarity to rotary collar magnets 170 (i.e., such as by a magnetic dipole-dipole interaction). When the rotary collar 225 is rotated, the magnetic attraction created between the rotary collar magnets 170 and the cannula magnets 150 facilitate rotation of the inner cannula 110 to release the proximal end of the prosthesis, as described in detail below.

The rotary dial 220 serves to limit the distal movement of the handle rear inner 215 and prevent the continued withdrawal of the sheath 120 until the rotary collar 225 has been fully rotated. The rotary dial 220 includes a movement slot 221, an engagement slot 222, and a tab 223 (FIG. 6). The movement slot 221 extends from the proximal end of the rotary dial 220, and allows the rotary dial 220 to accommodate and receive the tab 207 protruding from the inner surface of the first handle 205. The engagement slot 222 is located at the distal end of the rotary dial 220, adjacent to the distal end of the movement slot 221, and serves to lock the rotary dial 220 in place when tab 207 is rotated to fit into and engage slot 222. Tab 223 protrudes from the outside surface of the proximal end of the rotary dial 220 and engages slot 206 to prevent rotary dial 220 from sliding distally out of the back of distal end of the first handle 205.

A guide wire flush port 230 is located at the distal end of the inner cannula 110 and provides access to the guide wire flush tube (not shown) that is disposed about the cannula 110 and is connected to the positioner 330. As shown in FIG. 6, the positioner 330 is disposed about the inner cannula 110 and extends proximally from the proximal disk 259. The positioner 330 includes an attachment slot 331 that is configured to receive the tab 207 to retain the positioner 330 in a stationary position.

The sheath 120 extends from the proximal end 600 of the delivery device to the proximal end of the first handle 205. The proximal end of the handle rear inner 215 is attached to the distal end of the sheath 120 at sheath connector 245. The sheath connector 245 provides access to the sheath 120 for the positioner 330 and the sheath flush tube 235. The sheath flush tube 235 connects the sheath flush port 240 to the sheath connector 245. The sheath flush port 240 is flushed with saline when the delivery device is introduced into the patient's body.

As shown in FIGS. 6-10, one or more magnets within the handle assembly 200 facilitate rotation of the inner cannula 110 in response to manual rotation of the rotary collar 225. In one example, as shown in FIG. 10, a magnetic sub-assembly 100 within the handle assembly 200 includes magnets that are attached to, secured and/or embedded in the rotary collar 225 and also on the cannula 110. In particular, the magnetic sub-assembly comprises collar magnets 170 attached to the rotary collar 225 and cannula magnets 150 attached to the cannula 110.

More specifically, as shown in FIGS. 7 and 8, a square sleeve 160 is attached to the cannula 110, such as by soldering, crimping, adhesives and/or other suitable attachment methods or mechanisms. In one embodiment, the square sleeve 160 is made of stainless steel or nitinol, and alternatively, may be injection molded. The cannula magnets 150 are attached to or otherwise secured to the square sleeve 160 such as by soldering, adhesives, and the like, or, if the square sleeve 160 is stainless steel, by magnetic induction itself. In one example, a cannula magnet 150 is attached to each of the four sides of the square sleeve 160, but it is also contemplated that a cannula magnet 150 is attached to one or more sides, such as two opposite sides of the square sleeve 160. In one example, cannula magnets 150 are contained between the distal disk 258 and the proximal disk 259 on the cannula 110.

The handle rear inner 215 is disposed about the square sleeve 160 and cannula magnets 150, while the rotary collar 225 is disposed about a portion of the handle rear inner 215. In one example, as seen in FIG. 7, collar magnets 170 are attached to the inside surface of the rotary collar 225. In another configuration, as seen in FIGS. 8 and 9, collar magnets 170 are attached to a rotary collar magnet retention section 180 which is a space formed inside the rotary collar 225 to receive or otherwise to allow the placement of the collar magnet 170. FIGS. 7 and 8 illustrate the collar magnets 170 attached to the rotary collar 225 such that they are placed opposite or diametrically opposed to each other, however, collar magnets 170 may also be positioned in various other positions and/or in other arrangements on the rotary collar 225.

The handle rear inner 215 separates collar magnets 170 on the rotary collar 225 from the magnets 150 on the cannula 110. This creates a clearance between the rotary collar 225 and the cannula 110, allowing for rotational movement between the respective two components without magnets 150, 170 sticking together. As the physician rotates the rotary collar 225, the mechanical force between two nearby magnetized surfaces (e.g., the cannula magnets 150 magnetically attracted to the collar magnets 170, such as by dipole-dipole attraction) allow for 1:1 rotation of the square sleeve 160 connected to the cannula 110, thus, causing the cannula 110 to rotate, thereby releasing at least a portion of a prosthesis carried at the proximal end of the cannula 110. Attachment and release of the prosthesis carried on the cannula at the proximal end of the delivery device is described further below.

More particularly, FIGS. 13 and 14 illustrate a proximal portion of the delivery device 600, and one example of an attachment and release mechanism for the proximal end of a prosthesis using the delivery handle assembly 200 described herein. FIG. 13 shows a tapered nose cone 615 having a proximal tip 620 at the proximal end of the inner cannula 110. Nose cone 615 has a reverse distal taper 625 at its distal end 630. The nose cone surface 640 presents a smooth tapered surface to facilitate entry into and movement through a body vessel. An exemplary attachment and release mechanism 635 is disposed at or near the distal end 630 of the nose cone 615 and on the inner cannula 110. As shown in enlarged view in FIG. 12, the attachment and release mechanism 635 comprises coiled member 645 having a proximal end 650, a distal end 655, and a plurality of turns 660 disposed there between.

In one non-limiting example, the proximal end 650 of the coiled member 645 is secured to the outer surface 675 of the cannula 110 using a suitable attachment mechanism, such as a solder, weld, mechanical attachment, friction fit, crimp, or combination of these or other techniques. Accordingly, the proximal end 650 of the coiled member 645 cannot move relative to the outer surface 675 of the inner cannula 110. The proximal end 650 of the coiled member 645 comprises a first diameter d 1, which may be approximately the same diameter, or slightly greater than an outer diameter of the cannula 110.

The distal end 655 of the coiled member 645 is unsecured relative to the outer surface 675 of the inner cannula 110, as shown in FIG. 12. The distal end 655 of the coiled member 645 may comprise a second diameter d 2 which is greater than the first diameter d 1 of the proximal end 650 of the coiled member 645. There is a separation or gap 680 between the distal end 655 of the coiled member 645 and the outer surface 675 of the cannula 110.

The plurality of turns 660 are divided into a proximal series of turns 665, which have the first diameter d 1, and a distal series of turns 670, which have the second diameter d 2. The proximal series of turns 665 may be disposed in close proximity or abutting one another, as depicted in FIG. 12. By contrast, the distal series of turns 670 may be spaced apart from one another a greater distance than the proximal series of turns 665. In FIG. 12, the distal series of turns 670 are spaced apart a predetermined distance denoted by spacing 685.

As shown in FIGS. 13 and 14, prosthesis, such as stent graft 700, is disposed on the device and has a proximal end 710 and distal end 720. Stent graft 700 includes, in this example, a graft material 706, a bare proximal top stent 740 (though the disclosure is not so limited), and one or more stents 750 attached to the graft material 730. The stents 750 may be on either or both inner and outer surfaces of the tube of graft material 730 and may have the characteristics of self-expanding stents, balloon expanding stents, or both, depending on the desired stent characteristics.

As shown in FIG. 14, the stent graft 700 has an uncoupled state in which the stent graft 700 is positioned coaxially over the inner cannula 110 with the proximal end 710 of the stent graft 700 in longitudinal proximity relative to the distal end of the coiled member 645. During assembly, one or more loops 760 that are coupled to the proximal apices 770 of the bare proximal stent 740 are threaded around the distal end of the coiled member 645 one at a time. preferably until all of the loops 760 are coupled to the coiled member 645. Such coupling may be achieved by rotating the inner cannula 110 in a clockwise direction until the proximal end 710 of the stent 740 is sufficiently compressed in a radially inward direction, as depicted in FIG. 13. A gap 680 between the distal end of the coiled member 645 and the outer surface of the inner cannula 110 permits positioning of the loops 760 in the series of turns at the distal end of the coiled member 645. This type of attachment system of the proximal stent to the delivery system is more fully described with reference to FIGS. 4 and 5 of U.S. application Ser. No. 13/796,395 (filed Mar. 12, 2013) which description and Figures, and in particular FIGS. 1, 2, 4 and 5, are hereby incorporated by reference in their entirety.

The loops 760 are further accommodated within a spacing between the distal series of turns. The loops 760 preferably are coupled to the coiled member 645 in a manner in which at least one loop 760 is positioned around at least one full turn of the distal series of turns, and preferably around at least 1.5 turns at the distal end 655 of the coiled member 645, thereby reducing the likelihood of inadvertent uncoupling of the loops 760 from the coiled member 645.

The coupling shown in FIG. 13 secures the stent 740 to the cannula 110 via the coiled member 645 in a manner that may subsequently facilitate insertion of the subassembly comprising the inner cannula 110 and the stent graft 700 into an outer sheath, such as sheath 120 described above, as shown in FIG. 15. As will be apparent, the outer sheath 120 is configured to radially restrain other regions of the stent graft 700 for delivery to a target site within a patient's anatomy. The loops 760 may be coupled to every other proximal apex 770 as shown in FIG. 14 to restrain the stent 740 during delivery. In such a case, the loops 760 are not coupled to the second proximal apices 780, which may comprise barbs. By restraining the alternating proximal apices 770 using the loops 760 coupled to the coiled member 645, the adjacent second proximal apices 780 also may be indirectly pulled in a radially inward direction during delivery. The configuration of the stent 740 facilitates the indirect compression of the adjacent second proximal apices 780. Since only selected ones of the proximal apices are restrained during delivery, the number of loops 760 may be reduced. This type of attachment system of the proximal stent to the delivery system is more fully described with reference to FIGS. 4 and 5 of U.S. application Ser. No. 13/796,395 (filed Mar. 12, 2013) which description and Figures, and in particular FIGS. 1, 2, 4 and 5, are hereby incorporated by reference in their entirety.

One non-limiting example of a delivery and deployment sequence using a delivery device with deployment handle assembly 200 is now described and illustrated in FIGS. 13-19.

A delivery device may be initially flushed with saline through the flush port 240. A guide wire may then be introduced into the device though the distal end, allowing the device to be introduced into a patient's vasculature and tracked to a desired location. As shown in FIG. 15, a stent graft 700 is loaded on the cannula 110 at the proximal end of the delivery device and compressed by the sheath 120. FIGS. 1 and 2 show the deployment handle assembly 200 after the delivery device has been introduced into the patient's body and before any deployment steps have been performed. At this time, any safety latch 250 or other mechanism can be operated to "unlock" the handle assembly 200 to allow the handle assembly to be operated and a prosthesis deployment sequence to commence.

Next, the second handle 210 is pulled back in a distal direction along the outer surface of the first handle 205 as indicated by the arrow shown in FIG. 3. In operation, the physician places one hand (e.g., a "non-dominant" hand) on the front or first handle 205 and a second hand (e.g., a "dominant" hand) on the rear or second handle 210. The physician slowly pulls the second handle 210 in the distal direction with one hand as indicated by the arrow in FIG. 3, while the other hand gripping the first handle 205 stabilizes the device. Pulling back on the second handle 210 causes the attached sheath 120 to also retract in a distal direction indicated by the arrow shown in FIG. 16, thereby unsheathing at least a proximal portion of the prosthesis carried at the proximal end 600 of the delivery device. The positioner 330 preferably has sufficient rigidity and/or stiffness to resist buckling as the sheath 120 is retracted distally over it. The handle rear inner 215 moves distally as the second handle 210 is pulled back until the proximal lip 216 on the handle rear inner 215 hits the proximal end of the rotary dial 220, which prevents further distal movement of the handle rear inner 215 at this stage of deployment. This prevents the premature release of the distal attachment of the prosthesis. When the proximal lip 216 encounters the proximal end of the rotary dial 220, the second handle 210 is pulled back a sufficient distance to expose the rotary collar 225 as shown in FIGS. 3 and 4.

Figure 18:
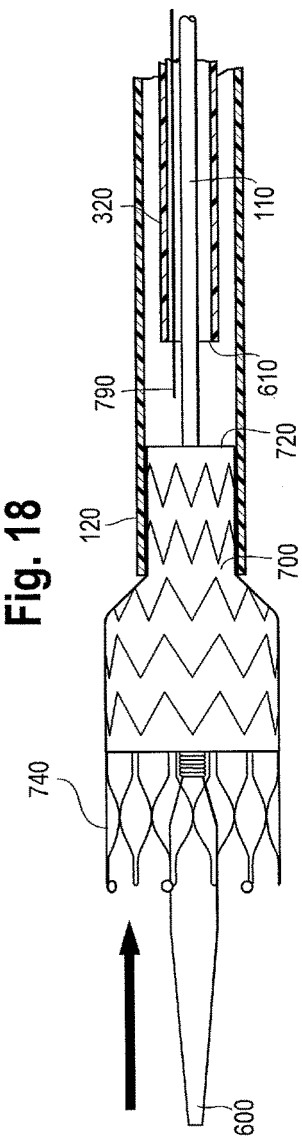
Figure 19:
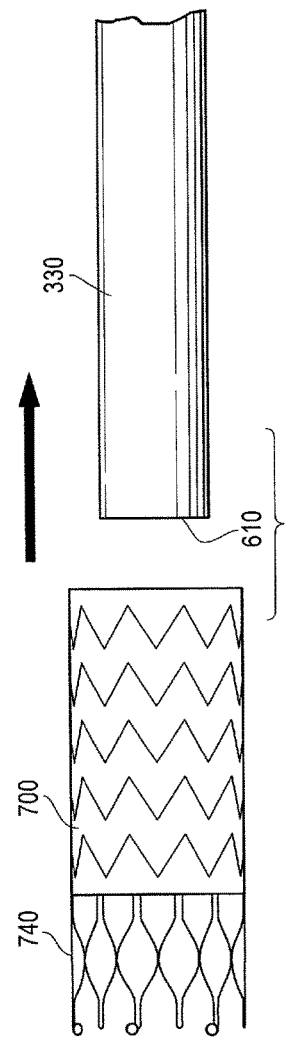

When the proximal top stent 740 is at least partially exposed, it is desirable to deploy the restrained proximal end of the stent 740. As shown in FIG. 4, the rotary collar 225 is now accessible to the physician and can be manually rotated, allowing the inner cannula 110 to be rotated in a counter-clockwise direction (as shown by the arrow in FIG. 17) until the loops 760 are uncoupled from the coiled member 645, i.e., in a reverse manner from which the loops 760 were coupled to the coiled member 645. Rotation of the inner cannula 110 thus releases the coiled member 645 from the proximal end of the prosthesis. The proximal stent 740 then may be deployed as shown in FIGS. 17, 18, and 19.

Until the rotary collar 225 is rotated to release the proximal end of the prosthesis, the physician cannot further pull back the second handle 210 to release of the distal end of the prosthesis (a deployment step illustrated in FIG. 5 and FIG. 18), thus preventing the various steps of deployment from being performed out of a preferred sequence.

In particular, as illustrated in FIG. 5, the collar threading 227 located at the proximal end of the rotary collar 225 is disposed about the dial threading 224 located at the distal end of the rotary dial 220. As the rotary collar 225 is rotated, the collar threading 227 and the dial threading 224 are engaged. The respective threading 227, 224 permits a selected number of rotations of the rotary collar 225 around the rotary dial 220 as the rotary dial 220 remains stationary. The selected number of rotations imparted to the rotary collar 225 is preferably the number of rotations required to rotate the cannula 110 to release the proximal end of the prosthesis.

When the rotary collar 225 has been sufficiently rotated about the rotary dial 220 such that release of the proximal end of the prosthesis from the coiled member 645 has been achieved, the rotary collar 225 can then be further rotated (e.g., one additional/final rotation) which imparts rotation to the rotary dial 220. This causes tab 207 to be released from the engagement slot 222 of the rotary dial 220 and move into the slot 221 of the rotary dial 220. In addition, the tab 223 on the proximal end of the rotary dial 220 is rotated into the rotary collar movement slot 206 of the first handle 205. This final rotation of the rotary dial 220 engages the rotary collar 225 and allows both the rotary collar 225 and the rotary dial 220 to be pulled back together in a distal direction with the second handle 210 as shown in FIG. 5.

In other words, the physician can now further pull back the second handle 210 to further retract the sheath 120 in a distal direction as shown by the arrow in FIG. 5. As the second handle 210 is pulled back, it also moves the handle rear inner 215 in a distal direction. The proximal lip 216 of the handle rear inner 215 engages the proximal end of the rotary dial 220 to also move the rotary dial 220 and the rotary collar 225 together in a distal direction. The rotary dial 220 is prevented from being entirely withdrawn out of the first handle 205 because tab 223, which protrudes from the rotary dial 220, is engaged with movement slot 206 (FIG. 6) formed in the distal end of the first handle 205.

FIGS. 18 and 19 illustrate the further release of the prosthesis from delivery device as the second handle 210 is further pulled back as shown in FIG. 5. Specifically, pulling back further on the second handle 210 further retracts the sheath 120 (as shown by the arrows in FIGS. 18, 19) and exposes the distal end of the prosthesis. The simultaneous withdrawal of the rotary dial 220 with the second handle 210 withdraws the cannula 110 distally from the body of the prosthesis and the withdrawal of the rotary collar 225 withdraws the trigger wire 790 from the distal end of the prosthesis to thereby release the prosthesis from the delivery device and deploy it within the body lumen at the desired deployment site.

The invention claimed is:

1. A prosthesis delivery device comprising:
   a rotatable inner cannula having a proximal end and a distal end;
   a prosthesis releasably coupled to the proximal end of the inner cannula, the inner cannula having a first position in which the prosthesis is retained on the cannula and a second position in which the prosthesis is released from the cannula;
   at least one magnet disposed on the rotatable inner cannula;
   a handle assembly disposed about a portion of the rotatable inner cannula, the handle assembly comprising a rotary collar having an inner surface, at least one magnet disposed on the inner surface of the rotary collar, wherein the at least one magnet disposed on the rotatable inner cannula and the at least one magnet disposed on the inner surface of the rotary collar comprise a magnetic attraction; and
   wherein the magnetic attraction translates torque from the rotation of the rotary collar to rotate the inner cannula from the first position to the second position to thereby release the prosthesis from the inner cannula.

2. The prosthesis delivery device of claim 1 further comprising a sleeve having an inner surface and an outer surface, wherein the inner surface of the sleeve is attached to the rotatable inner cannula.

3. The prosthesis delivery device of claim 2 wherein the at least one magnet disposed on the rotatable inner cannula is attached to the outer surface of the sleeve.

4. The prosthesis delivery device of claim 2 wherein the sleeve has a polygonal cross section, and wherein the at least one magnet disposed on the rotatable inner cannula is secured to at least one of the sides of the polygon.

5. The prosthesis delivery device of claim 2 wherein the sleeve has a square cross sectional shape and wherein the at least one magnet disposed on the rotatable inner cannula is secured to at least one of the sides of the square.

6. The prosthesis delivery device of claim 1 wherein the rotary collar comprises at least two diametrically opposed magnets attached to the inside surface of the rotary collar.

7. The prosthesis delivery device of claim 1 wherein the prosthesis comprises a stent graft having a stent at the proximal end thereof and wherein the stent comprises a series of proximal apices.

8. The prosthesis delivery device of claim 7 wherein the proximal end of the inner cannula comprises a coil that releasably engages one or more of the stent proximal apices.

9. A method of releasing a prosthesis from a delivery device, the delivery device comprising a rotatable inner cannula having a proximal end and a distal end and at least one magnet disposed on the inner cannula; a prosthesis releasably engaged with the proximal end of the inner cannula; a handle assembly disposed about a portion of the rotatable inner cannula, the method comprising:
   retracting a portion of the handle assembly to expose a proximal portion of the prosthesis;
   rotating a rotary collar within the handle assembly, the rotary collar comprising at least one magnet disposed on an inner surface thereof, wherein a magnetic attraction between the at least one magnet disposed on the inner surface of the rotary collar and the at least one magnet disposed on the inner cannula translates torque from the rotation of the rotary collar to rotate the inner cannula to thereby release a proximal portion of the prosthesis; and
   further retracting the portion of the handle assembly to thereby release a distal portion of the prosthesis.

* * * * *